United States Patent
Narimatsu et al.

(10) Patent No.: US 10,159,414 B2
(45) Date of Patent: Dec. 25, 2018

(54) PERIPHERAL VASCULAR RESISTANCE MEASURING DEVICE AND METHOD FOR CONTROLLING THE SAME

(71) Applicant: TERUMO KABUSHIKI KAISHA, Tokyo (JP)

(72) Inventors: Kiyoyuki Narimatsu, Shizuoka (JP); Takashi Morita, Saitama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 747 days.

(21) Appl. No.: 14/750,449

(22) Filed: Jun. 25, 2015

(65) Prior Publication Data

US 2015/0289771 A1    Oct. 15, 2015

Related U.S. Application Data

(63) Continuation of application No. PCT/JP2012/008317, filed on Dec. 26, 2012.

(51) Int. Cl.

| A61B 6/00 | (2006.01) |
|---|---|
| A61B 5/0205 | (2006.01) |
| A61B 5/02 | (2006.01) |
| A61B 5/00 | (2006.01) |
| A61B 5/024 | (2006.01) |

(Continued)

(52) U.S. Cl.
CPC ...... *A61B 5/02055* (2013.01); *A61B 5/02007* (2013.01); *A61B 5/02433* (2013.01); *A61B 5/6824* (2013.01); *A61B 5/742* (2013.01); *A61B 5/01* (2013.01); *A61B 5/0245* (2013.01); *A61B 5/0285* (2013.01); *A61B 5/02125* (2013.01);

(Continued)

(58) Field of Classification Search
CPC .......... A61B 5/01; A61B 5/00; A61B 5/02055
See application file for complete search history.

(56) References Cited

U.S. PATENT DOCUMENTS

| 6,126,595 A * | 10/2000 | Amano | A61B 5/02 |
| | | | 600/300 |
| 2003/0109791 A1* | 6/2003 | Kondo | A61B 5/021 |
| | | | 600/500 |

(Continued)

FOREIGN PATENT DOCUMENTS

| JP | H11-155826 | 6/1999 |
| JP | 2004/201868 | 7/2004 |
| JP | 2004/321253 | 11/2004 |

OTHER PUBLICATIONS

International Search Report for International (PCT) Patent Application No. PCT/JP2012/008317, dated Mar. 26, 2013, with translation, 3 pages.

(Continued)

*Primary Examiner* — Joel F Brutus
(74) *Attorney, Agent, or Firm* — Jason H. Vick; Sheridan Ross, PC (57) ABSTRACT

The difference between a skin temperature measured by a wrist sensor and a skin temperature measured by a finger sensor is calculated. A pulse wave transmission time from the wrist to the finger is obtained from a pulse wave measured by the wrist sensor and a pulse wave measured by the finger sensor. The product of the difference and the pulse wave transmission time is obtained as a peripheral vascular resistance on the peripheral side from the wrist.

20 Claims, 7 Drawing Sheets (51) Int. Cl.
  *A61B 5/0245*  (2006.01)
  *A61B 5/01*  (2006.01)
  *A61B 5/021*  (2006.01)
  *A61B 5/0285*  (2006.01)

(52) U.S. Cl.
  CPC .......... *A61B 5/6826* (2013.01); *A61B 5/6829* (2013.01); *A61B 2560/0475* (2013.01)

(56) References Cited

U.S. PATENT DOCUMENTS

2007/0112259 A1\* 5/2007 Tateda ............... A61B 5/02007
                                                                600/310
2007/0225606 A1\* 9/2007 Naghavi ............... A61B 5/015
                                                                600/438

OTHER PUBLICATIONS

Written Opinion of the International Search Report for International (PCT) Patent Application No. PCT/JP2012/008317, dated Mar. 26, 2013, with translation, 8 pages.
International Preliminary Report on Patentability for International (PCT) Patent Application No. PCT/JP2012/008317, dated Mar. 26, 2013, with translation, 6 pages.

\* cited by examiner

FIG. 7

PERIPHERAL VASCULAR RESISTANCE MEASURING DEVICE AND METHOD FOR CONTROLLING THE SAME

CROSS REFERENCE TO RELATED APPLICATIONS

This Application is a continuation of and claim priority to PCT/JP2012/008317, filed Dec. 26, 2012, entitled "PERIPHERAL VASCULAR RESISTANCE MEASUREMENT DEVICE AND METHOD FOR CONTROLLING THE SAME," which is incorporated herein by reference in its entirety for all that it teaches and for all purposes.

TECHNICAL FIELD

The present invention relates to techniques for measuring the peripheral vascular resistance from the wrist to the tip.

BACKGROUND ART

There are various techniques for measuring biological information of a patient. For example, Patent Literature 1 discloses techniques for easily measuring central side pulse wave propagation velocity information and peripheral side pulse wave propagation velocity information.

CITATION LIST

Patent Literature

Patent Literature 1: JP 3988674 B1

SUMMARY OF INVENTION

Technical Problem

A specialized heat adjustment system in a vascular system which plays a significant role in heat adjustment is localized only in an anatomically distal skin area, in particular, apart having no body hair such as the palm. This is an adjustment system by contraction and expansion of blood vessels centered on arteriovenous anastomoses (AVA). The AVA serve as shunts from arterioles to venules, which enables rapid heat exchange. When the AVA are open, the AVA blood flow is 10,000 times faster than the blood flow velocity in capillary vessels.

The heat exchange system centered on the AVA is mainly controlled by the sympathetic nervous system. When the whole body requests heat exchange/dissipation and control is performed as requested, the skin temperature in the palm increases compared to the skin temperature in the other part. On the other hand, the skin temperature in the palm decreases to prevent heat dissipation.

The applicant of this application has focused on such a principle and conceived measuring the skin temperature and the volume pulse wave as biological information in the finger of the hand and the wrist part which has relatively less fluctuation in the skin temperature and the volume pulse wave to determine sleepiness, poor blood circulation, autonomic imbalance, a sleeping state, and the like using the measured biological information.

Solution to Problem

In order to achieve the object of the present invention, for example, a peripheral vascular resistance measuring device of the present invention is connected to a wrist sensor which is attached to a wrist of a patient for measuring a skin temperature and a pulse wave in the wrist and a finger sensor which is attached to a finger of the patient for measuring a skin temperature and a pulse wave in the finger and includes:

means for calculating a difference between the skin temperature measured by the wrist sensor and the skin temperature measured by the finger sensor;

means for obtaining a pulse wave transmission time from the wrist to the finger from the pulse wave measured by the wrist sensor and the pulse wave measured by the finger sensor; and calculation means for obtaining a product of the difference and the pulse wave transmission time as a peripheral vascular resistance on a peripheral side from the wrist.

Advantageous Effects of Invention

The configuration of the present invention makes it possible to measure the skin temperature and the volume pulse wave as biological information in the finger of the hand and the wrist part which has relatively less fluctuation in the skin temperature and the volume pulse wave to determine sleepiness, poor blood circulation, autonomic imbalance, a sleeping state, and the like using the measured biological information.

The other features and advantages of the present invention will become apparent from the following description with reference to the accompanying drawings. Identical reference signs designate identical or similar elements throughout the accompanying drawings.

BRIEF DESCRIPTION OF DRAWINGS

The accompanying drawings are included in the specification, constitute apart of the specification, illustrate embodiments of the present invention, and used for describing the principle of the present invention together with the description of the embodiments.

DESCRIPTION OF EMBODIMENTS

Hereinbelow, preferred embodiments of the present invention will be described with reference to the accompanying drawings. Each of the embodiments described below shows an example when the present invention is embodied and is a specific embodiment of the configuration described in the claims.

First Embodiment

As described above, the applicant of this application has conceived measuring the skin temperature and the volume pulse wave as biological information in the finger of the hand and the wrist part which has relatively less fluctuation in the skin temperature and the volume pulse wave to determine sleepiness, poor blood circulation, autonomic imbalance, a sleeping state, and the like using the measured biological information. The difference between the skin temperature in the finger of the hand and the skin temperature in the wrist represents the amount of blood in the periphery such as capillary vessels, arterioles, and AVA. The difference between the volume pulse wave in the finger of the hand and the volume pulse wave in the wrist (a propagation time of the volume pulse wave from the wrist to the finger) represents tension/relaxation of large arteries equal to or larger than arterioles. Thus, in the present embodiment, these differences are used to obtain the resistance from the wrist to the periphery (peripheral vascular resistance). Various physical conditions of the patient can be inferred from the peripheral vascular resistance. Thus, in the present embodiment, information corresponding to the obtained peripheral vascular resistance is further notified to the patient.

First, an example of the configuration of a peripheral vascular resistance measuring device according to the present embodiment will be described with reference to FIG. 1. The peripheral vascular resistance measuring device according to the present embodiment includes a finger sensor 103 which is a sensor to be attached to the finger of a hand 150 of a patient, a wrist sensor 105 which is a sensor to be attached to the wrist of the patient, and a main body 100. The main body 100 is connected to the finger sensor 103 through a wire 104 and connected to the wrist sensor 105 through a wire 106. It is needless to say that wireless connection may be used instead of using the wires 104 and 106. Although, in the description with reference to FIG. 1 and the other drawings, the wrist sensor 105 is attached to the wrist of the right hand and the finger sensor 103 is attached to the forefinger of the right hand, the hand and the finger to which the sensors are attached are not limited to the right hand and the forefinger.

Figure 2:
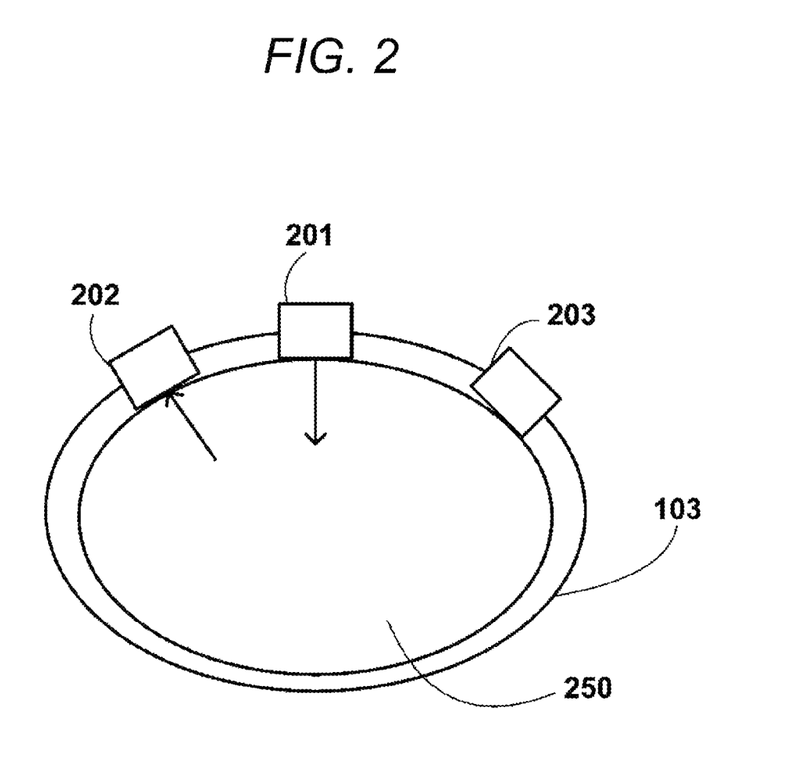
FIG. 2 is a cross-sectional view of the finger with a finger sensor 103 attached and the finger sensor 103.

First, the finger sensor 103 will be described. The finger sensor 103 is attached to the finger of a patient and used for measuring the skin temperature of the finger and the pulse wave in the finger. FIG. 2 is a cross-sectional view of the finger with the finger sensor 103 attached and the finger sensor 103. The cross section of the finger is denoted by 250. As illustrated in FIG. 2, the finger sensor 103 is attached to the finger. A light emitter 201 which emits infrared rays, a light receiver 202 which receives the infrared rays, and a sensor 203 which measures the temperature are attached to the finger sensor 103.

The light emitter 201 and the light receiver 202 together constitute a pulse wave sensor. Infrared rays emitted by the light emitter 201 are reflected inside the finger and the reflected infrared rays are received by the light receiver 202. When the amount of blood inside the finger is large, infrared rays emitted by the light emitter 201 are absorbed by hemoglobin in the blood. As a result, the reflection amount of infrared rays is reduced, and the light receiving amount in the light receiver 202 is also reduced. On the other hand, when the amount of blood inside the finger is small, the amount of hemoglobin is also small. As a result, the reflection amount of infrared rays increases, and the light receiving amount in the light receiver 202 also increases. That is, since the pulse wave (pulse) is related to an increase/decrease of the light receiving amount in the light receiver 202, the pulse wave (pulse) can be determined from a time series of the light receiving amount in the light receiver 202.

Since a method and principle for measuring the pulse wave using a pulse wave sensor is known, further description will be omitted.

The light receiver 202 sends a signal indicating the light receiving amount, that is, a waveform signal of the pulse wave (the signal indicating the light receiving amount may be appropriately processed into a waveform signal of the pulse wave) to the main body 100 through the wire 104. The main body 100 records the signal received from the light receiver 202 in a RAM 502 as data.

The main body 100 controls the operation (start and finish of light emission, for example) of the light emitter 201 through the wire 104.

The sensor 203 is a temperature sensor such as a thermistor. The sensor 203 measures the skin temperature of the finger and sends a signal indicating the measured skin temperature to the main body 100 through the wire 104.

Figure 3:
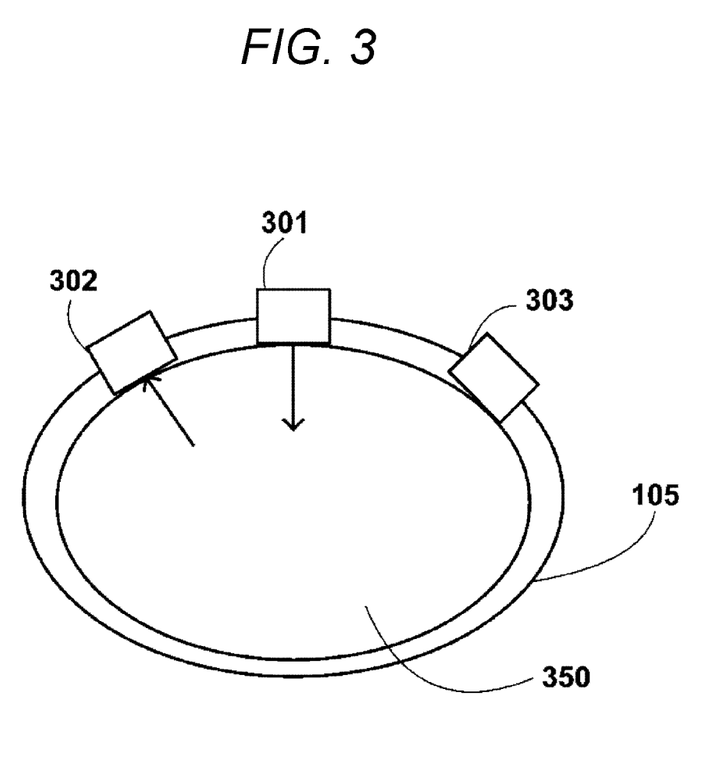
FIG. 3 is a cross-sectional view of the wrist with a wrist sensor 105 attached and the wrist sensor 105.

Next, the wrist sensor 105 will be described. The wrist sensor 105 is attached to the wrist of the patient and used for measuring the skin temperature of the wrist and the pulse wave in the wrist. FIG. 3 is a cross-sectional view of the wrist with the wrist sensor 105 attached and the wrist sensor 105. The cross section of the wrist is denoted by 350. As illustrated in FIG. 3, the wrist sensor 105 is attached to the wrist. A light emitter 301 which emits infrared rays, a light receiver 302 which receives the infrared rays, and a sensor 303 which measures the temperature are attached to the wrist sensor 105. The light emitter 301 and the light receiver 302 together constitute a pulse wave sensor. The operation of the light emitter 301 is similar to the operation of the light emitter 201, and the operation of the light receiver 302 is similar to the light receiver 202. Specifically, the pulse wave in the wrist is measured, and a waveform signal of the measured pulse wave is sent to the main body 100 through the wire 106. The main body 100 controls the operation of the light emitter 301 through the wire 106.

The sensor 303 is a temperature sensor such as a thermistor. The sensor 303 measures the skin temperature of the wrist and transmits a signal indicating the measured skin temperature to the main body 100 through the wire 106.

Next, the main body 100 will be described. The main body 100 is provided with a liquid crystal screen 101 and a button 102 which can be depressed by a user. An example of the hardware configuration of the main body 100 will be described with reference to a block diagram of FIG. 5.

Figure 5:
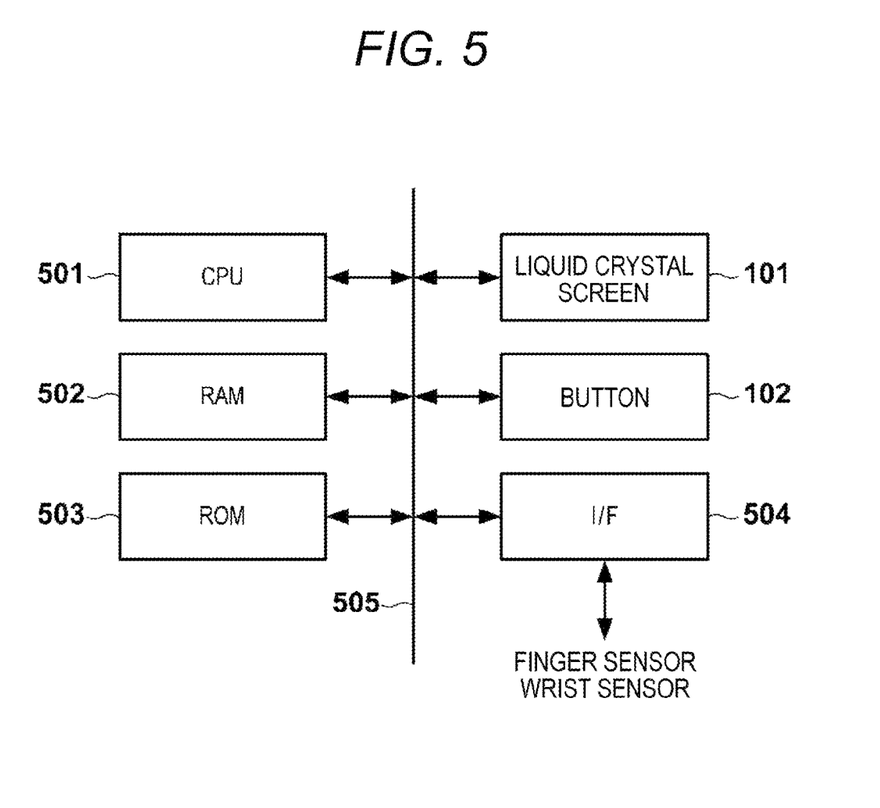
FIG. 5 is a block diagram illustrating an example of the hardware configuration of a main body 100.

A CPU 501 executes processing using a computer program and data stored in the RAM 502 and a ROM 503 to control the operation of the entire main body 100 and also control the operations of the finger sensor 103 and the wrist sensor 105 which are connected to an I/F 504 through the wires 104 and 106.

The RAM 502 has an area for temporarily storing data corresponding to a signal sent from the finger sensor 103 or the wrist sensor 105 and a work area used by the CPU 501 for executing various kinds of processing.

A computer program and data for allowing the CPU 501 to execute each processing (which will be described below as processing performed by the main body 100) are stored in the ROM 503. The computer program and data stored in the ROM 503 are appropriately loaded into the RAM 502 in accordance with control performed by the CPU 501 so as to be a target of processing executed by the CPU 501.

The liquid crystal screen 101 is a screen capable of displaying a result of the processing executed by the CPU 501 using an image or a character. The button 102 is depressed by a user for inputting various instructions. A signal indicating the depression of the button 102 is notified to the CPU 501 from the button 102.

All the members described above are connected to a bus 505.

Figure 6:
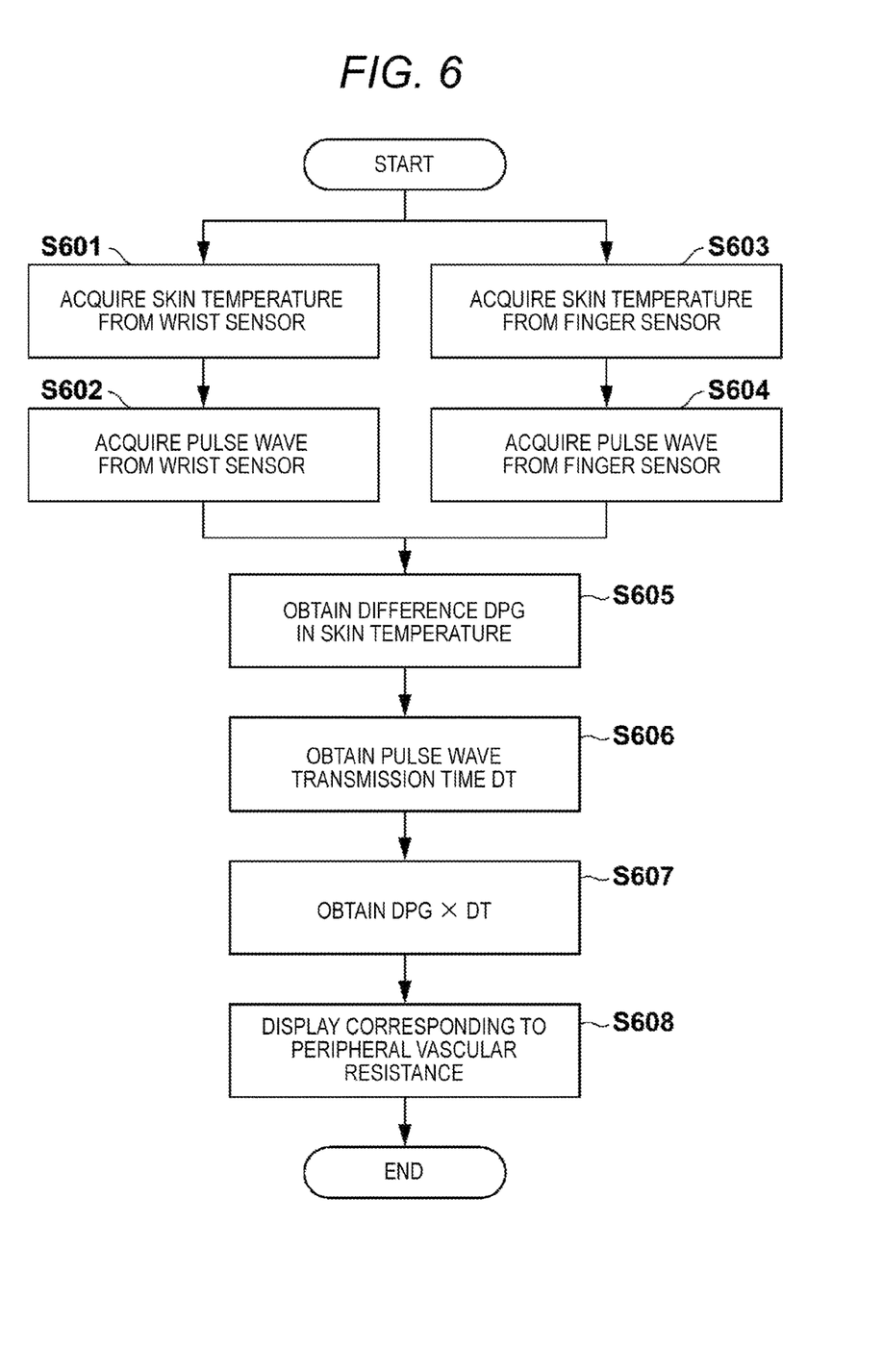
FIG. 6 is a flowchart of the operation of the main body 100.

Next, the operation of the main body 100 will be described with reference to a flowchart of FIG. 6. A computer program and data for allowing the CPU 501 to execute processing in accordance with the flowchart of FIG. 6 are stored in the ROM 503. Thus, the CPU 501 loads the computer program and data from the ROM 503 into the RAM 502 and executes the processing using the loaded computer program and data to thereby execute the processing in accordance with the flowchart of FIG. 6.

Processing in step S601 and step S602 and processing in step S603 and step S604 are performed in parallel. The wrist sensor 105 operates synchronously with the finger sensor 103.

In step S601, the CPU 501 stores a signal of the skin temperature received from the sensor 303 provided in the wrist sensor 105 through the I/F 504 in the RAM 502 as data.

In step S602, the CPU 501 stores a waveform signal of the pulse wave received from the light receiver 302 provided in the wrist sensor 105 through the I/F 504 in the RAM 502 as data.

In step S603, the CPU 501 stores a signal of the skin temperature received from the sensor 203 provided in the finger sensor 103 through the I/F 504 in the RAM 502 as data.

In step S604, the CPU 501 stores a waveform signal of the pulse wave received from the light receiver 202 provided in the finger sensor 103 through the I/F 504 in the RAM 502 as data.

In step S605, the CPU 501 obtains a difference DPG between the data of the skin temperature of the wrist stored in the RAM 502 in step S601 and the data of the skin temperature of the skin temperature of the finger stored in the RAM 502 in step S603 (the difference between the skin temperature in the wrist and the skin temperature in the finger).

In step S606, the CPU 501 obtains a pulse wave transmission time DT between the wrist and the finger using the data of the pulse wave of the wrist and the data of the pulse wave of the finger stored in the RAM 502. This processing will be described with reference to FIG. 4.

Figure 4:
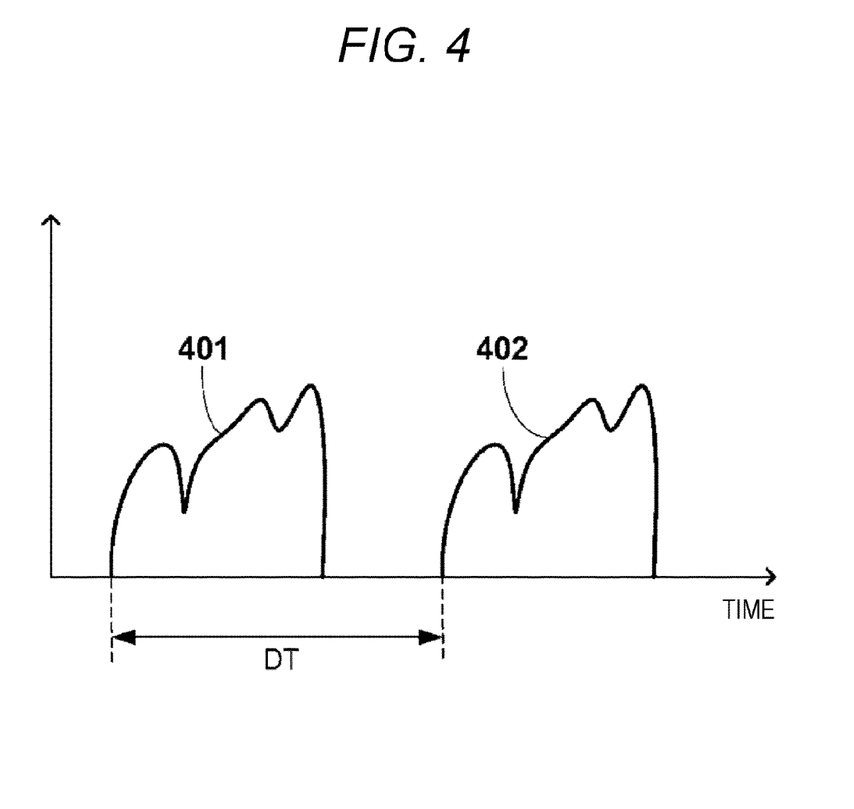
FIG. 4 is a diagram describing processing for obtaining a pulse wave transmission time DT.

In FIG. 4, the horizontal axis represents time. FIG. 4 illustrates a pulse wave 401 measured by the wrist sensor 105 and a pulse wave 402 measured by the finger sensor 103. As illustrated in FIG. 4, in terms of time, the pulse wave is first observed in the wrist, and then observed in the finger. Thus, for example, the difference between a rising start timing of the pulse wave 402 and a rising start timing of the pulse wave 401 is obtained as the pulse wave transmission time DT between the wrist and the finger. It is needless to say that a method for obtaining the pulse wave transmission time is not limited to this method.

It is to be noted that, when the difference DPG is the difference between a skin temperature measured by the sensor 203 and a skin temperature measured by the sensor 303 at a time t1, the pulse wave transmission time DT is the difference between a rising start timing of the pulse wave 401 at a time near the time t1 and a rising start timing of the pulse wave 402 at the nearest time after the rising start timing of the pulse wave 401.

In step S607, the CPU 501 obtains the product of the difference DPG and the pulse wave transmission time DT as the peripheral vascular resistance on the peripheral side from the wrist. Then, in step S608, the CPU 501 reads information corresponding to the obtained peripheral vascular resistance from the ROM 503 and displays a screen based on the read information on the liquid crystal screen 101.

For example, when the peripheral vascular resistance is relatively high (equal to or higher than a threshold), it is recognized that the patient is in a state including arteriolar level relaxation and AVA/capillary opening and sleepiness/sleep is in an initial state. On the other hand, when the peripheral vascular resistance is relatively low (lower than the threshold), it is recognized that the patient is in a state including arterial level tension and AVA/capillary tension, in a situation including tension of sympathetic nerves, high blood pressure, and a tendency to suffer from cardiovascular accident, and has vascular endothelial dysfunction. Thus, information associating the peripheral vascular resistance with a health state of the patient corresponding thereto is previously stored in the ROM 503. In step S608, a state of the patient corresponding to the peripheral vascular resistance obtained in step S607 is read from the ROM 503 and the read state is displayed on the liquid crystal screen 101. Character information or an image representing the state of the patient may be displayed.

Modification 1

A method which obtains the product of an average value of the DPG within a certain time and an average value of the DT within the certain time as the peripheral vascular resistance may be employed as another method for obtaining the peripheral vascular resistance. In this case, for example, the CPU 501 may obtain an average value of the DPG and an average value of the DT within a certain time after depression of the button 102 by the patient and calculate the product of the obtained average values as the peripheral vascular resistance. Then, information corresponding to the calculated peripheral vascular resistance may be presented to the patient in the same manner as in the first embodiment.

Second Embodiment

In the first embodiment, information corresponding to the peripheral vascular resistance is presented. However, information corresponding to a combination of the DPG and the DT may be presented. In this case, for example, as illustrated in FIG. 7, a table in which information corresponding to each combination of the DPG and the DT is registered may be previously registered in the ROM 503.

Figure 7:
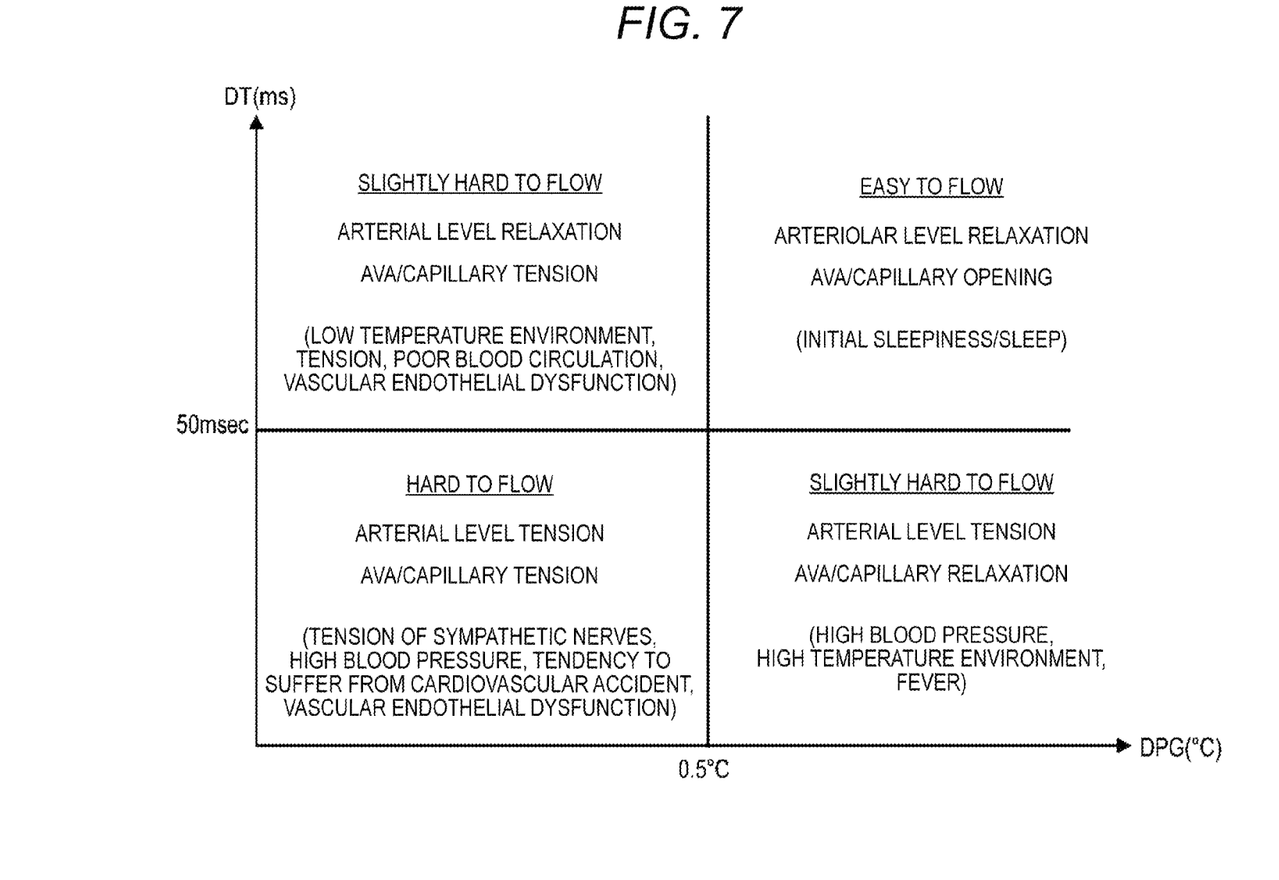
FIG. 7 is a diagram illustrating an example of the configuration of a table in which information corresponding to each combination of DPG and DT is registered.

In the case of FIG. 7, when the DPG is 0.5° C. or more and the DT is 50 ms or more, arteriolar level relaxation and AVA/capillary opening are determined, and sleepiness/sleep is determined to be an initial state. When the DPG is 0.5° C. or more and the DT is less than 50 ms, arterial level tension and AVA/capillary relaxation are determined, and high blood pressure, a high temperature environment, and fever are determined. When the DPG is less than 0.5° C. and the DT is 50 ms or more, arterial level relaxation and AVA/capillary tension are determined, and a low temperature environment, tension, poor blood circulation, and vascular endothelial dysfunction are determined. When the DPG is less than 0.5° C. and the DT is less than 50 ms, arterial level tension and AVA/capillary tension are determined, and tension of sympathetic nerves, high blood pressure, a tendency to suffer from cardiovascular accident, and vascular endothelial dysfunction are determined.

The configuration of the table in FIG. 7 is merely an example, and various configurations are conceivable. Further, the above thresholds, specifically, "0.5° C." and "50 ms" in the table of FIG. 7 are also merely examples, and may be modified in each situation and each person.

As described above in the first embodiment, a form of displaying a result of the determination on the liquid crystal screen 101 may be display using character information or an image corresponding to the result. Further, the determination result may be recorded as a history in a memory device which can be connected to the RAM 502 and the main body 100, and the history may be displayed later on a display screen of an external device which can be connected to the liquid crystal screen 101 and the main body 100.

Third Embodiment

Figure 1:
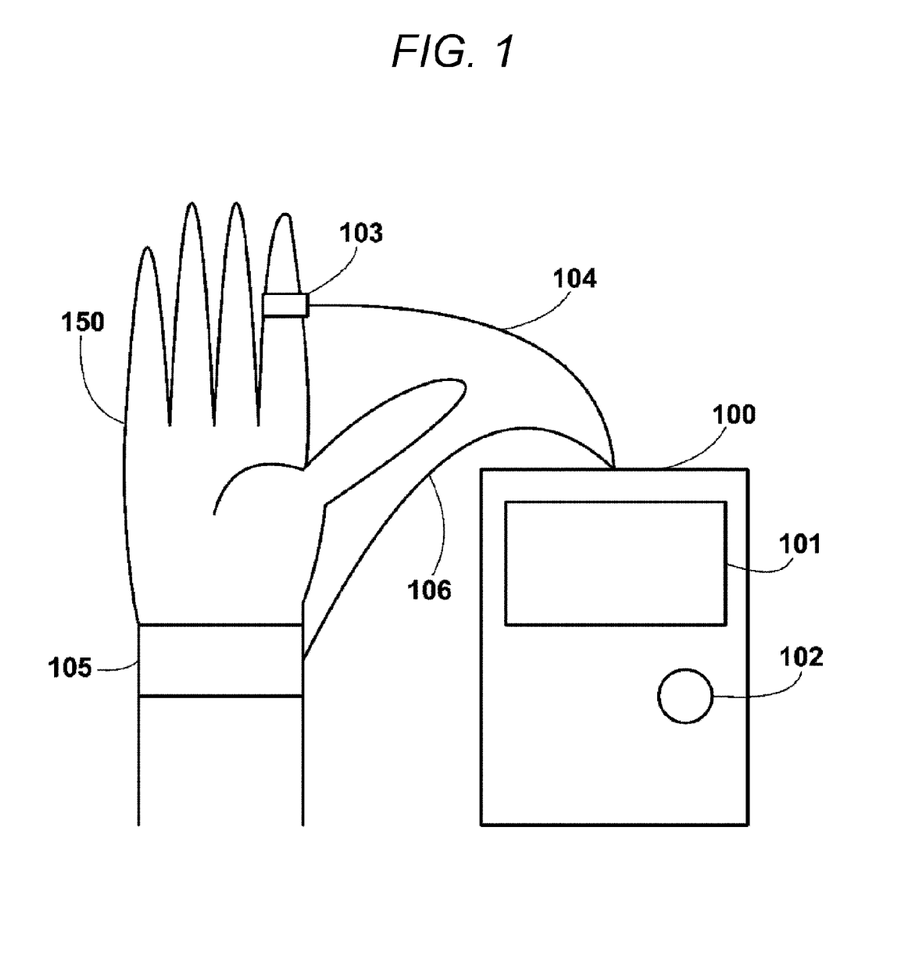
FIG. 1 is a diagram illustrating an example of the configuration of a peripheral vascular resistance measuring device.

In the configuration of the peripheral vascular resistance measuring device illustrated in FIG. 1, the main body 100 is a device separate from the wrist sensor 105 and the finger sensor 103. However, the main body 100 may be incorporated in the wrist sensor 105 or the finger sensor 103. That is, the peripheral vascular resistance measuring device may include the finger sensor 103 and the wrist sensor 105 in which the main body 100 is incorporated or may include the wrist sensor 105 and the finger sensor 103 in which the main body 100 is incorporated.

Further, various configurations are conceivable as the configuration of the main body 100. Thus, the configuration of the main body 100 is not necessarily limited to the configuration illustrated in FIG. 5. For example, when information notification corresponding to the peripheral vascular resistance or a combination of the DPG and the DT is performed using sound, it is necessary to add a configuration for performing sound output to the main body 100.

Whether to perform information notification corresponding to the peripheral vascular resistance or information notification corresponding to a combination of the DPG and the DT may be set by operating the button 102 by a user.

The present invention is not limited to the above embodiments. Various changes and modifications can be made without departing from the spirit and scope of the invention. Therefore, the following claims are appended to disclose the scope of the invention.

The invention claimed is:

1. A peripheral vascular resistance measuring device connected to a wrist sensor attached to a wrist of a patient for measuring a skin temperature and a pulse wave in the wrist and a finger sensor attached to a finger of the patient for measuring a skin temperature and a pulse wave in the finger, the peripheral vascular resistance measuring device comprising a processor and a memory including instructions stored thereon that, when executed by the processor, cause the processor to:
 determine a difference between the skin temperature measured by the wrist sensor and the skin temperature measured by the finger sensor;
 determine a pulse wave transmission time from the wrist to the finger based on a propagation time from the pulse wave measured by the wrist sensor and the pulse wave measured by the finger sensor; and
 determine a product of the difference and the pulse wave transmission time as a peripheral vascular resistance on a peripheral side from the wrist.

2. The peripheral vascular resistance measuring device according to claim 1, further comprising a display screen for display-outputting a health state of the patient corresponding to the peripheral vascular resistance or a combination of the difference and the pulse wave transmission time.

3. The peripheral vascular resistance measuring device according to claim 2, wherein each of the wrist sensor and the finger sensor has a pulse wave sensor, which includes a set of a light emitters that emit infrared rays and a light receiver that receives the infrared rays, and a temperature sensor or thermistor, and wherein the peripheral vascular resistance measuring device measures the pulse wave by the pulse wave sensor and the skin temperature by the temperature sensor.

4. The peripheral vascular resistance measuring device according to claim 1, wherein determining the product of the difference and the pulse wave transmission time includes determining a product of an average value of the difference within a time period and an average value of the pulse wave transmission time within the time period as the peripheral vascular resistance on the peripheral side from the wrist.

5. A method for controlling a peripheral vascular resistance measuring device connected to a wrist sensor attached to a wrist of a patient for measuring a skin temperature and a pulse wave in the wrist and a finger sensor attached to a finger of the patient for measuring a skin temperature and a pulse wave in the finger, the method comprising the steps of:
 determining a difference between the skin temperature measured by the wrist sensor and the skin temperature measured by the finger sensor;
 determining a pulse wave transmission time from the wrist to the finger based on a propagation time from the pulse wave measured by the wrist sensor and the pulse wave measured by the finger sensor; and
 determining a product of the difference and the pulse wave transmission time as a peripheral vascular resistance on a peripheral side from the wrist.

6. The method according to claim 5, wherein each of the wrist sensor and the finger sensor has a pulse wave sensor which includes a set of a light emitters that emit infrared rays and a light receiver that receives the infrared rays and a temperature sensor or thermistor, and wherein the peripheral vascular resistance measuring device measures the pulse wave by the pulse wave sensor and the skin temperature by the temperature sensor.

7. The method according to claim 5, wherein the skin temperature measured by the wrist sensor or the skin temperature measured by the finger sensor is measured at a time T1, which corresponds to a rise in the pulse wave.

8. The method according to claim 7, further comprising:
 storing, in a memory of the peripheral vascular resistance measuring device, the difference between the skin temperature measured by the wrist sensor and the skin temperature measured by the finger sensor; and
 storing, in the memory of the peripheral vascular resistance measuring device, the pulse wave transmission time from the wrist to the finger based on the propagation time from the pulse wave measured by the wrist sensor to be measured by the finger sensor.

9. The method according to claim 5, further comprising:
 storing, in a memory of the peripheral vascular resistance measuring device, two or more pulse wave transmission times from two or more measurements conducted at two or more different times; and
 storing, in the memory of the peripheral vascular resistance measuring device, two or more differences in skin temperature as measured by the wrist sensor and the finger sensor from two or more measurements conducted at two or more different times.

10. The method according to claim 9, further comprising:
 determining an average value for the two or more of the pulse wave transmission times; and determining an average value for the two or more differences in skin temperature as measured by the wrist sensor and the finger sensor.

11. The method according to claim 10, further comprising determining a product of the difference in skin temperature and the pulse wave transmission time as a peripheral vascular resistance based on the determined average values for the two or more differences in skin temperature and the pulse wave transmission times.

12. A device comprising:
a wrist sensor that measures a first skin temperature and a pulse wave at a wrist of a subject;
a finger sensor that measures a second skin temperature and the pulse wave at a finger of the subject; and
a main body comprising a processor and a memory including instructions stored thereon that, when executed by the processor, cause the processor to:
receive the first and second skin temperatures from the wrist sensor and finger sensor;
receive the pulse wave measurements from the wrist sensor and finger sensor;
determine a difference between the first skin temperature measured by the wrist sensor and the second skin temperature measured by the finger sensor;
determine a pulse wave transmission time from the wrist to the finger based on a propagation time from the pulse wave measured by the wrist sensor and the pulse wave measured by the finger sensor; and
determine a product of the difference in skin temperatures and the pulse wave transmission time as a peripheral vascular resistance on a peripheral side from the wrist.

13. The device according to claim 12, wherein the wrist sensor and the finger sensor each comprises:
a temperature sensor; and
a pulse wave sensor.

14. The device according to claim 13, wherein the pulse wave sensor comprises:
an infrared light emitter; and
an infrared light receiver.

15. The device according to claim 12, wherein the memory of the main body comprises: a Read Only Memory (ROM) that stores the instructions associated with operating the device.

16. The device according to claim 15, wherein the main body comprises: a Random Access Memory (RAM) operable to store one or more of the first skin temperature, the second skin temperature, the pulse wave measurement from the wrist sensor, the pulse wave measurement from the finger sensor, the difference between the first skin temperature measured by the wrist sensor and the second skin temperature measured by the finger sensor, the pulse wave transmission time from the wrist to the finger from the pulse wave measured by the wrist sensor and the pulse wave measured by the finger sensor, and the peripheral vascular resistance on a peripheral side from the wrist.

17. The device according to claim 16, wherein the RAM is operable to store two or more instances of one or more of the first skin temperature, the second skin temperature, the pulse wave measurement from the wrist sensor, the pulse wave measurement from the finger sensor, the difference between the first skin temperature measured by the wrist sensor and the second skin temperature measured by the finger sensor, and the pulse wave transmission time from the wrist to the finger from the pulse wave measured by the wrist sensor and the pulse wave measured by the finger sensor.

18. The device according to claim 17, wherein the processor is in communication with the ROM and the RAM, the processor operable to determine an average value of the peripheral vascular resistance on a peripheral side from the wrist based on the two or more instances of one or more of the first skin temperature, the second skin temperature, the pulse wave measurement from the wrist sensor, the pulse wave measurement from the finger sensor, the difference between the first skin temperature measured by the wrist sensor and the second skin temperature measured by the finger sensor, and the pulse wave transmission time from the wrist to the finger from the pulse wave measured by the wrist sensor and the pulse wave measured by the finger sensor.

19. The device according to claim 18, further comprising a display screen in communication with the processor, the display screen operable to display the determined peripheral vascular resistance on a peripheral side from the wrist.

20. The device according to claim 19, wherein the display screen is further operable to display a condition of the subject based on the peripheral vascular resistance on a peripheral side from the wrist.

* * * * *